(12) United States Patent
Johnston et al.

(10) Patent No.: US 6,521,235 B2
(45) Date of Patent: *Feb. 18, 2003

(54) ALPHAVIRUS RNA REPLICON SYSTEMS

(75) Inventors: Robert E. Johnston, Chapel Hill, NC (US); Nancy L. Davis, Chapel Hill, NC (US); Jonathan F. Smith, Cary, NC (US); Peter Pushko, Frederick, MD (US); Michael Parker, Frederick, MD (US); George Ludwig, Frederick, MD (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/803,600

(22) Filed: Mar. 9, 2001

(65) Prior Publication Data

US 2001/0016199 A1 Aug. 23, 2001

Related U.S. Application Data

(63) Continuation of application No. 09/620,311, filed on Jul. 20, 2000, which is a continuation of application No. 08/981,159, filed on Nov. 10, 1997, which is a continuation of application No. PCT/US96/07454, filed on May 21, 1996, which is a continuation-in-part of application No. 08/448,630, filed on May 23, 1995, now Pat. No. 5,792,462, application No. 09/803,600, which is a continuation-in-part of application No. 09/598,569, filed on Jun. 21, 2000, which is a continuation of application No. 09/122,286, filed on Jul. 24, 1998, now Pat. No. 6,156,558, which is a continuation of application No. 08/448,630, filed on May 23, 1995, now Pat. No. 5,792,462.

(51) Int. Cl.$^7$ .................... A61K 39/12; C12N 7/01; C12N 15/86

(52) U.S. Cl. ............... 424/199.1; 424/218.1; 435/235.1; 435/236; 435/320.1

(58) Field of Search .............. 435/235.1, 236, 435/320.1; 424/199.1, 218.1

(56) References Cited

U.S. PATENT DOCUMENTS

| | | |
|---|---|---|
| 4,650,764 A | 3/1987 | Temin et al. |
| 5,091,309 A | 2/1992 | Schlesinger et al. |
| 5,185,440 A | 2/1993 | Davis et al. |
| 5,217,879 A | 6/1993 | Huang et al. |
| 5,505,947 A | 4/1996 | Johnston et al. |
| 5,639,650 A | 6/1997 | Johnston et al. |
| 5,643,576 A | 7/1997 | Johnston et al. |
| 5,739,026 A | 4/1998 | Garoff et al. ............. 435/320.1 |
| 5,766,602 A | 6/1998 | Xiong et al. ............. 424/218.1 |
| 5,789,245 A | 8/1998 | Dubensky et al. ........ 435/320.1 |
| 5,792,462 A | 8/1998 | Johnston et al. ......... 424/199.1 |
| 5,814,482 A | 9/1998 | Dubensky, Jr. et al. .... 435/69.3 |
| 5,843,723 A | 12/1998 | Dubensky, Jr. et al. .... 435/69.3 |
| 6,015,694 A | 1/2000 | Dubensky et al. ......... 435/69.3 |
| 6,156,558 A * | 12/2000 | Johnston et al. ......... 435/235.1 |
| 6,190,666 B1 | 2/2001 | Garoff et al. ............. 424/208.1 |

FOREIGN PATENT DOCUMENTS

| | | | |
|---|---|---|---|
| WO | WO 92/10578 | 6/1992 | |
| WO | WO 95/07994 | 3/1995 | |
| WO | WO 95/27044 | 10/1995 | |
| WO | WO 95/31565 | 11/1995 | |
| WO | WO 96/17072 | 6/1996 | |
| WO | WO 96/37220 | 11/1996 | .......... A61K/39/12 |
| WO | WO 96/37616 | 11/1996 | |
| WO | WO 00/39318 | 7/2000 | .......... C12N/15/86 |

OTHER PUBLICATIONS

Bredenbeek et al, *Sindbis Virus Expression Vectors: Packaging of RNA Replicons by Using Defective Helper RNAs*, Journal of Virology 67 No. 11, pp. 6439–3446 (1993).

Corsini, et al.: *Efficiency of Transduction by Recombinant Sindbis Replicon Virus Varies Among Cell Lines, Including Mosquito Cells and Rat Sensory Neurons*, BioTechniques, 21:3 (492–497), Sep. 1996.

Davis et al., *Attenuating Mutations in the E2 Glycoprotein Gene of Venezuelan Equine Encephalitis Virus: Construction of Single and Multiple Mutants in a Full–Length cDNA Clone*, Virology 183 20–31 (1991).

Davis et al, *A Genetically Engineered Live Virus Vaccine for Venezuelan Equine Encephalitis*; J. Cell Biochemistry Supplement O No. 17 Part D, issued 1993, Abstract N404.

Davis et al, Virology 212:102–110 (1995).

Frolov et al., *Alphavirus–based expression vectors: Stategies and applications*, Proc. Natl. Acad. Sci. USA, vol. 93, pp. 11371–11377 (1996).

Grieder et al., *Specific Restrictions in the Progression of Venezuelan Equine Encephalitis Virus–Induced Disease Resulting from Single AminoAcid Changes in the Glycoproteins*, Virology, 206, pp. 994–1006 (1995).

Lemm et al., *Polypeptide requirements for assembly of functional Sindbis virus replication complexes: a model for the temporal regulation of minus– and plus–strand RNA synthesis*, The EmBO Journal, vol. 13, No. 12, pp. 2925–2934 (1994).

(List continued on next page.)

*Primary Examiner*—Mary E. Mosher
(74) *Attorney, Agent, or Firm*—Myers Bigel Sibley & Sajovec, P.A.

(57) ABSTRACT

The present invention provides a helper cell for expressing an infectious, replication defective, alphavirus particle in an alphavirus-permissive cell. The helper cell includes (a) a first helper RNA encoding (i) at least one alphavirus structural protein, and (ii) not encoding at least one alphavirus structural protein; and (b) a second helper RNA separate from the first helper RNA, the second helper RNA (i) not encoding the alphavirus structural protein encoded by the first helper RNA, and (ii) encoding the at least one alphavirus structural protein not encoded by the first helper RNA. Preferably, the helper cell is co-transfected with a replicon RNA encoding an alphavirus packaging segment and an inserted heterogeneous RNA, such that all of the alphavirus structural proteins assemble together into alphavirus particles in the cell, with said replicon RNA packaged therein.

78 Claims, 2 Drawing Sheets

OTHER PUBLICATIONS

Liljestrom et al., *A New Generation of Animal Cell Expression Vectors Based on the Semliki Forest Virus Replicon,* Bio/Technology, vol. 9, Dec. 1991, pp. 1356–1361.

Morgenstein et al, *Advanced mammalian gene transfer: high titre retroviral vectors with multiple drug selection markers and a complementary helper-free packaging cell line,* Nucleic Acids Research 18:No. 12, pp. 3587–3596 (1990).

J.M. Polo and R.E. Johnston, *Attenuating Mutations in Glycoproteins E1 and E2 of Sindbis Virus Produce a Highly Attenuated Strain When Combined in Vitro,* Journal of Virology 64 No. 9, pp. 4438–4444 (1990).

Russell et al., *Sindbis Virus Mutations Which Coordinately Affect Glycoprotein Processing, Penetration, and Virulence in Mice,* Journal of Virology, vol. 63, No. 4, Apr. 1989, pp. 1619–1629.

R.J. Schoepp and R.E. Johnston, *Directed Mutagenesis of a Sindbis Virus Pathogenesis Site;* Virology 193, pp. 149–159 (1993).

Simpson, et al., *Complete Nucleotide Sequence and Full–Length cDNA clone of S.A.AR86, a South African Alphavirus Related to Sindbis*[1], Virology 222 (464–469) Article No. 0445, 1996.

Strauss et al., *The Alphaviruses: Gene Expression, Replication, and Evolution,* Microbiological Reviews, Sep. 1994, pp. 491–562.

Suomalainen et al., *Spike Protein–Nucleocapsid Interactions Drive the Budding of Alphaviruses,* J. Virology, vol. 66, No. 8, pp. 4737–4747 (1992).

Cheng Xiong, et al. "Sindbis Virus: An Efficient, Broad Host Range Vector for Gene Expression in Animal Cells." *Science,* New Series, vol. 243, Issue 4895 (Mar. 3, 1989), 1188–1191.

Ute Geigenmuller–Gnirke, et al. "Complementation Between Sindbis Viral RNAs Produces Infectious Particles with a Bipartite Genome." *Proceedings of the National Academy of Sciences of the United States of America,* vol. 88, Issue 8 (Apr. 15, 1991), 3253–3257.

Barbara G. Weiss and Sondra Schlesinger. "Recombination between Sindbis Virus RNAs". *Journal of Virology.* vol. 65, No. 8 (Aug. 1991), 4017–4025.

Sondra Shclesinger. "Alphaviruses—vectors for the expression of heterologous genes." *TiBTech.* (1993), 18–22.

Richard M. Kinney. "Attenuation of Venzuelan Equine Encephalitis Virus Strain TC–83 Is Encoded by the 5'–Noncoding Region and the E2 Envelope Glycoprotein." *Journal of Virology.* vol. 67, No. 3, (Mar. 1993), 1269–1277.

N.L. Davis. "A molecular genetic approach to the study of Venezuelan equine encephalitis virus pathogenesis." *Archives of Virology.* (1994), 99–109.

E. Mathilda Sjöberg, et al. "A Significantly Improved Semliki Forest Virus Expression System Based on Translation Enhancer Segments from the Viral Capsid Gene." *Bio/Technology.* vol. 12, (Nov. 1994), 1127–1131.

Peter Liljeström. "Alphavirus expression systems." *Current Opinion in Biotechnology.* vol. 5, No. 5, (Oct. 1994), 495–500.

S. Schlesinger and B.G. Weiss. "Recombination between Sindbis virus RNAs." *Archives of Virology.* Suppl. 9, (1994), 213–220.

* cited by examiner

FIG. 3A

MOUSE 1; INOCULATION WITH $4 \times 10^5$

- ○ ANTIBODY TO LASSA N
- ■ ANTIBODY TO VEE

ELISA TITER vs DAYS POST INOCULATION

BOOSTER INJECTION

FIG. 3B

MOUSE 2; INOCULATION WITH $4 \times 10^7$

- ○ ANTIBODY TITER TO LASSA N
- ■ ANTIBODY TITER TO VEE

ELISA TITER vs DAYS POST INOCULATION

BOOSTER INJECTION

ALPHAVIRUS RNA REPLICON SYSTEMS

RELATED APPLICATION INFORMATION

This application is a continuation of U.S. application Ser. No. 09/620,311, filed Jul. 20, 2000, which is a continuation of U.S. application Ser. No. 08/981,159, filed Nov. 10, 1997 (now allowed), which is a continuation under 35 U.S.C. § 371 of PCT Application No. PCT/US96/07454, filed on May 21, 1996, which is a continuation-in-part of co-pending U.S. application Ser. No. 08/448,630, filed on May 23, 1995, which issued as U.S. Pat. No. 5,792,462; the disclosures of which are incorporated by reference herein in their entireties.

This application is also a continuation-in-part of co-pending U.S. application Ser. No. 09/598,569, filed Jun. 21, 2000, which is a continuation of U.S. application Ser. No. 09/122,286, filed on Jul. 24, 1998, which issued as U.S. Pat. No. 6,156,558, which is a continuation of U.S. application Ser. No. 08/448,630, filed on May 23, 1995, which issued as U.S. Pat. No. 5,792,462, the disclosures of which are incorporated by reference herein in their entireties.

STATEMENT OF FEDERAL SUPPORT

This invention was made with federal support under Grant numbers DAMD17-91-C-1092 and 9113-ARG-0610 from the Department of the Army. The government has certain rights to this invention.

FIELD OF THE INVENTION

The present invention relates to recombinant DNA technology, and in particular to introducing and expressing foreign genes in a eukaryotic cell.

BACKGROUND OF THE INVENTION

The Alphavirus genus includes a variety of viruses all of which are members of the Togaviridae family. The alphaviruses include Eastern Equine Encephalitis virus (EEE), Venezuelan Equine Encephalitis virus (VEE), Everglades virus, Mucambo virus, Pixuna virus, Western Equine Encephalitis virus (WEE), Sindbis virus, Semliki Forest virus, Middelburg virus, Chikungunya virus, O'nyong-nyong virus, Ross River virus, Barmah Forest virus, Getah virus, Sagiyama virus, Bebaru virus, Mayaro virus, Una virus, Aura virus, Whataroa virus, Babanki virus, Kyzylagach virus, Highlands J virus, Fort Morgan virus, Ndumu virus, and Buggy Creek virus. The viral genome is a single-stranded, messenger-sense RNA, modified at the 5'-end with a methylated cap, and at the 3'-end with a variable-length poly (A) tract. Structural subunits containing a single viral protein, C, associate with the RNA genome in an icosahedral nucleocapsid. In the virion, the capsid is surrounded by a lipid envelope covered with a regular array of transmembranal protein spikes, each of which consists of a heterodimeric complex of two glycoproteins, E1 and E2. See Pedersen et al., *J. Virol.* 14:40 (1974). The Sindbis and Semliki Forest viruses are considered the prototypical alphaviruses, and have been studied extensively. See Schlesinger, *The Togaviridae and Flaviviridae*, Plenum Publishing Corp., New York (1986). The VEE virus has been studied by the present inventors. See U.S. Pat. No. 5,185,440 to Davis et al.

The study of these viruses has led to the development of beneficial techniques for vaccinating against the alphavirus diseases, and other diseases through the use of alphavirus vectors for the introduction of foreign DNA. See U.S. Pat. No. 5,185,440 to Davis et al., and PCT Publication WO 92/10578. The introduction of foreign DNA into eukaryotic cells has become a topic of increasing interest. It is well known that live, attenuated viral vaccines are among the most successful means of controlling viral disease. However, for some virus pathogens, immunization with a live virus strain may be either impractical or unsafe. One alternative strategy is the insertion of sequences encoding immunizing antigens of such agents into a vaccine strain of another virus. One such system utilizing a live VEE vector is described in U.S. Pat. No. 5,505,947 to Johnston et al. Another such system is described by Hahn et al., *Proc. Natl. Acad. Sci. USA* 89:2679 (1992), wherein Sindbis virus constructs which express a truncated form of the influenza hemagglutinin protein are described. Unfortunately, relatively few such systems are currently available.

Accordingly, there remains a need in the art for nucleic acid sequences encoding foreign antigens to be safely incorporated into a vaccine strain of a virus, which may be then be utilized as a vaccine for the foreign antigen.

SUMMARY OF THE INVENTION

As a first aspect, the present invention provides a helper cell for expressing an infectious, replication defective, alphavirus particle in an alphavirus-permissive cell. The helper cell includes (a) a first helper RNA encoding (i) at least one alphavirus structural protein, and (ii) not encoding at least one alphavirus structural protein; and (b) a second helper RNA separate from the first helper RNA, the second helper RNA (i) not encoding the at least one alphavirus structural protein encoded by the first helper RNA, and (ii) encoding at least one alphavirus structural protein not encoded by the first helper RNA, such that the alphavirus structural proteins assemble together into alphavirus particles in the cell. Preferably, the alphavirus packaging segment is deleted from at least the first helper RNA, and is more preferably deleted from both the first helper RNA and second helper RNA.

In a preferred embodiment, the helper cell is co-transfected with a replicon RNA, which encodes the alphavirus packaging segment and an inserted heterologous RNA. In the embodiment wherein the helper cell also includes a replicon RNA, the alphavirus packaging segment may be, and preferably is, deleted from both the first helper RNA and the second helper RNA. For example, in the embodiment wherein the helper cell includes a replicon RNA encoding the alphavirus packaging segment and an inserted heterologous RNA, the first helper RNA encodes the alphavirus E1 glycoprotein and the alphavirus E2 glycoprotein, and the second helper RNA encodes the alphavirus capsid protein. The replicon RNA, first helper RNA, and second helper RNA are all on separate molecules and are co-transfected into the host cell.

In an alternative embodiment, the helper cell includes a first helper RNA encoding the alphavirus E1 glycoprotein and the alphavirus E2 glycoprotein, and is co-transfected with a replicon RNA encoding the alphavirus packaging segment, an inserted heterologous RNA, and the remaining alphavirus structural proteins not encoded by a first helper RNA. Thus, the replicon RNA and the first helper RNA are on separate molecules, and the replicon RNA and the RNA encoding a structural protein not encoded by the first helper RNA are on a single molecule. The heterologous RNA comprises a foreign RNA which encodes for proteins or peptides which are desirably expressed in the helper cell.

The RNA encoding the structural proteins, i.e., the first helper RNA and the second helper RNA, may advantageously include one or more attenuating mutations. In the preferred embodiment, at least one of the first helper RNA and the second helper RNA includes at least one attenuating mutation. The attenuating mutations provide the advantage that in the event of RNA recombination within the cell, the conjoining of the structural and non-structural genes will produce a virus of decreased virulence.

As a second aspect, the present invention provides a method of making infectious, replication defective, alphavirus particles. The method includes co-transfecting a helper cell as given above with a replicon RNA, producing the alphavirus particles in the transfected cell, and then collecting the alphavirus particles from the cell. The replicon RNA encodes the alphavirus packaging segment, non-structural proteins and a heterologous RNA. The non-structural proteins encoded by the replicon RNA may be such proteins as are required for replication and transcription. The transfected cell further includes the first helper RNA and second helper RNA as described above.

As a third aspect, the present invention provides a set of RNAs for expressing an infectious, replication defective alphavirus. The set of RNAs comprises, in combination, (a) a replicon RNA encoding a promoter sequence, an inserted heterologous RNA, wherein RNA encoding at least one structural protein of the alphavirus is deleted from the replicon RNA, and (b) a first helper RNA separate from the replicon RNA, wherein the first helper RNA encodes in trans, the structural protein which is deleted from the replicon RNA, and a promoter sequence. In this embodiment, it is preferred that an RNA segment encoding at least one of the structural proteins is located on an RNA other than the first helper RNA. Thus, for example, the set of RNAs may include a replicon RNA including RNA which encodes the alphavirus packaging sequence, the inserted heterologous RNA, and the alphavirus capsid protein, but both the alphavirus E1 glycoprotein and alphavirus E2 glycoprotein are deleted therefrom; and a first helper RNA includes RNA encoding both the alphavirus E1 glycoprotein and the alphavirus E2 glycoprotein.

In another embodiment, the set of RNAs also includes a second helper RNA separate from the replicon RNA and the first helper RNA. In this embodiment, the second helper RNA encodes, in trans, at least one structural protein, which is different from the structural protein encoded by the replicon RNA and by the first helper RNA. Thus, for example, the set of RNAs may include a replicon RNA including RNA which encodes the alphavirus packaging sequence, and the inserted heterologous RNA: a first helper RNA including RNA which encodes a promoter sequence and an RNA encoding both the alphavirus E1 glycoprotein and the alphavirus E2 glycoprotein; and a second helper RNA including a promoter sequence and RNA which encodes the alphavirus capsid protein, with the replicon RNA, the first helper RNA, and the second helper RNA being in trans from each other, on separate molecules.

As a fourth aspect, the present invention provides infectious VEE replicon particles containing RNA encoding a promoter sequence, and an inserted heterologous RNA, and wherein RNA encoding at least one alphavirus structural protein is deleted from the RNA so that the infectious virus particle is replication defective.

As a fifth aspect, the present invention provides a pharmaceutical formulation comprising infectious alphavirus particles as described above, in an effective immunogenic amount in a pharmaceutically acceptable carrier.

The foregoing and other aspects of the present invention are explained in detail in the detailed description set forth below.

BRIEF DESCRIPTION OF THE DRAWINGS

FIG. 2 also illustrates a single helper RNA system plasmid, and the construction of recombinant VEE clones containing heterologous genes.

FIG. 3 is a graphical representation of the results obtained in inoculating mice with the VEE replicon/Lassa N infectious particles produced by a single-helper RNA system, at two different dosage units. The top graph (FIG. 3A) represents results obtained with a low-dose inoculation with infectious particles. The bottom graph (FIG. 3B) illustrates results obtained with a high-dose inoculation with infectious particles.

DETAILED DESCRIPTION OF THE INVENTION

Figure 1:
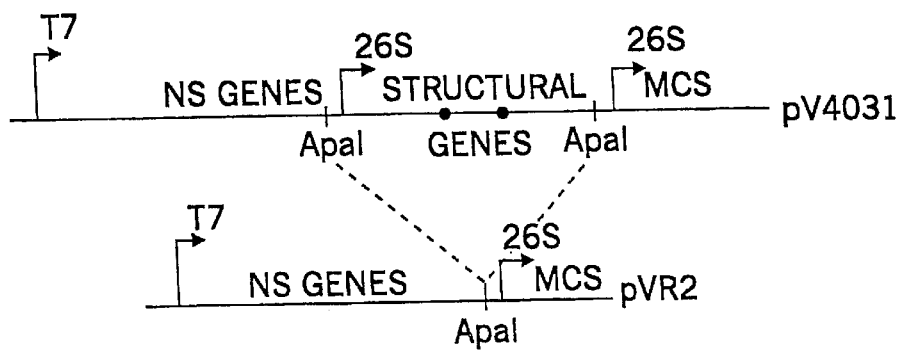
FIG. 1 is a graphical representation of the pV4031 clone and the production of the pVR2 clone.

The term "alphavirus" has its conventional meaning in the art, and includes the various species of alphaviruses such as Eastern Equine Encephalitis virus (EEE), Venezuelan Equine Encephalitis virus (VEE), Everglades virus, Mucambo virus, Pixuna virus, Western Equine Encephalitis virus (WEE), Sindbis virus, South African Arbovirus No. 86, Semliki Forest virus, Middelburg virus, Chikungunya virus, O'nyong-nyong virus, Ross River virus, Barmah Forest virus, Getah virus, Sagiyama virus, Bebaru virus, Mayaro virus, Una virus, Aura virus, Whataroa virus, Babanki virus, Kyzylagach virus, Highlands J virus, Fort Morgan virus, Ndumu virus, Buggy Creek virus, and any other virus classified by the International Committee on Taxonomy of Viruses (ICTV) as an alphavirus. The preferred alphavirus RNA transcripts for use in the present invention include VEE, Sindbis virus, South African Arbovirus No. 86, and Semliki Forest virus.

Alphavirus-permissive cells employed in the methods of the present invention are cells which, upon transfection with the viral RNA transcript, are capable of producing viral particles. Alphaviruses have a broad host range. Examples of suitable host cells include, but are not limited to Vero cells, baby hamster kidney (BHK) cells, and chicken embryo fibroblast cells.

The phrases "structural protein" or "alphavirus structural protein" as used herein refer to the encoded proteins which are required for encapsidation (e.g., packaging) of the RNA replicon, and include the capsid protein, E1 glycoprotein, and E2 glycoprotein. As described hereinabove, the structural proteins of the alphavirus are distributed among one or more helper RNAs (i.e., a first helper RNA and a second helper RNA). In addition, one or more structural proteins may be located on the same RNA molecule as the replicon RNA, provided that at least one structural protein is deleted from the replicon RNA such that the resulting alphavirus particle is replication defective. As used herein, the terms "deleted" or "deletion" mean either total deletion of the specified segment or the deletion of a sufficient portion of the specified segment to render the segment inoperative or nonfunctional, in accordance with standard usage. See, e.g., U.S. Pat. No. 4,650,764 to Temin et al. The term "replication defective" as used herein, means that the replicon RNA cannot be encapsidated in the host cell in the absence of the helper RNA. The resulting alphavirus particles are replication defective inasmuch as the replicon RNA does not include all of the alphavirus structural proteins required for encapsidation, at least one of the required structural proteins being deleted therefrom, such that the packaged replicon RNA is not capable of replicating the entire viral genome.

The helper cell for expressing the infectious, replication defective alphavirus particle comprises a set of RNAs, as described above. The set of RNAs principally include a first helper RNA and a second helper RNA. The first helper RNA includes RNA encoding at least one alphavirus structural protein but does not encode all alphavirus structural proteins. In other words, the first helper RNA does not encode at least one alphavirus structural protein; the at least one non-coded alphavirus structural protein being deleted from the first helper RNA. In one embodiment, the first helper RNA includes RNA encoding the alphavirus E1 glycoprotein, with the alphavirus capsid protein and the alphavirus E2 glycoprotein being deleted from the first helper RNA. In another embodiment, the first helper RNA includes RNA encoding the alphavirus E2 glycoprotein, with the alphavirus capsid protein and the alphavirus E1 glycoprotein being deleted from the first helper RNA. In a third, preferred embodiment, the first helper RNA includes RNA encoding the alphavirus E1 glycoprotein and the alphavirus E2 glycoprotein, with the alphavirus capsid protein being deleted from the first helper RNA.

The second helper RNA includes RNA encoding at least one alphavirus structural protein which is different from the at least one structural protein encoded by the first helper RNA. Thus, the second helper RNA encodes at least one alphavirus structural protein which is not encoded by the first helper RNA. The second helper RNA does not encode the at least one alphavirus structural protein which is encoded by the first helper RNA, thus the first and second helper RNAs do not encode duplicate structural proteins. In the embodiment wherein the first helper RNA includes RNA encoding only the alphavirus E1 glycoprotein, the second helper RNA may include RNA encoding one or both of the alphavirus capsid protein and the alphavirus E2 glycoprotein which are deleted from the first helper RNA. In the embodiment wherein, the first helper RNA includes RNA encoding only the alphavirus E2 glycoprotein, the second helper RNA may include RNA encoding one or both of the alphavirus capsid protein and the alphavirus E1 glycoprotein which are deleted from the first helper RNA. In the embodiment wherein the first helper RNA includes RNA encoding both the alphavirus E1 glycoprotein and the alphavirus E2 glycoprotein, the second helper RNA may include RNA encoding the alphavirus capsid protein which is deleted from the first helper RNA.

In one embodiment, the packaging segment (RNA comprising the encapsidation or packaging signal) is deleted from at least the first helper RNA. In a preferred embodiment, the packaging segment is deleted from both the first helper RNA and the second helper RNA.

In the preferred embodiment wherein the packaging segment is deleted from both the first helper RNA and the second helper RNA, the helper cell is co-transfected with a replicon RNA in addition to the first helper RNA and the second helper RNA. The replicon RNA encodes the packaging segment and an inserted heterologous RNA. The inserted heterologous RNA may be RNA encoding a protein or a peptide. Typically, the inserted heterologous RNA encodes a protein or a peptide which is desirably expressed by the host alphavirus-permissive cell, and includes the promoter and regulatory segments necessary for the expression of that protein or peptide in that cell. The inserted heterologous RNA may encode any protein or peptide that may be desirably produced by the host cell. Suitable heterologous RNA may be of prokaryotic (e.g., RNA encoding the Botulinus toxin C), or eukaryotic (e.g., RNA from *Aqueoria victoria* jellyfish encoding the green fluorescent protein (GFP), RNA encoding malaria Plasmodium protein cs1) origin.

Additionally, inserted heterologous RNA suitable in the practice of the present invention include viral RNA from a wide variety of viruses including, but not limited to, Arenaviruses (e.g., Lassa fever virus), Lentiviruses (e.g., HIV, SIV, Equine infectious anemia virus), Poxviruses (e.g., Vaccinia), Filoviruses (e.g., Ebola virus, Marburg virus), Orthomyxoviruses (e.g., Influenza virus), Bunyaviruses (e.g., RVFV, CCHF, and SFS viruses), and Coronaviruses. Examples of suitable viral RNA genes that may be used to provide the inserted heterologous RNA include, but are not limited to the Lassa fever virus nucleocapsid protein gene, the Lassa fever envelope glycoprotein gene, the influenza hemagglutinin gene, the influenza nucleoprotein gene, the human coronavirus envelope glycoprotein gene, the HIV envelope GP160 gene, and the HIV matrix/capsid gene. The replicon RNA also encodes the alphavirus nonstructural proteins, including cis-acting sequences required for replication and transcription.

In a preferred embodiment, the replicon RNA, the first helper RNA and the second helper RNA are provided on separate molecules such that a first molecule, i.e., the replicon RNA, includes RNA encoding the packaging segment and the inserted heterologous RNA, a second molecule, i.e., the first helper RNA, includes RNA encoding at least one but not all of the required alphavirus structural proteins, and a third molecule, i.e., the second helper RNA, includes RNA encoding at least one but not all of the required alphavirus structural proteins. For example, in one preferred embodiment of the present invention, the helper cell includes a set of RNAs which include (a) a replicon RNA including RNA encoding an alphavirus packaging sequence and an inserted heterologous RNA, (b) a first helper RNA including RNA encoding the alphavirus E1 glycoprotein and the alphavirus E2 glycoprotein, and (c) a second helper RNA including RNA encoding the alphavirus capsid protein so that the alphavirus E1 glycoprotein, the alphavirus E2 glycoprotein and the capsid protein assemble together into alphavirus particles in the host cell.

In an alternate embodiment, the replicon RNA and the first helper RNA are on separate molecules, and the replicon RNA and RNA encoding a structural gene not encoded by the first helper RNA are on another single molecule together, such that a first molecule, i.e., the first helper RNA, including RNA encoding at least one but not all of the required alphavirus structural proteins, and a second molecule, i.e., the replicon RNA, including RNA encoding the packaging segment, the inserted heterologous RNA, and the remaining structural proteins not encoded by the first helper RNA. For example, in one preferred embodiment of the present invention, the helper cell includes a set of RNAs including (a) a replicon RNA including RNA encoding an alphavirus packaging sequence, an inserted heterologous RNA, and an alphavirus capsid protein, and (b) a first helper RNA including RNA encoding the alphavirus E1 glycoprotein and the alphavirus E2 glycoprotein so that the alphavirus E1 glycoprotein, the alphavirus E2 glycoprotein and the capsid protein assemble together into alphavirus particles in the host cell, with the replicon RNA packaged therein.

In one preferred embodiment of the present invention, the RNA encoding the alphavirus structural proteins, i.e., the capsid, E1 glycoprotein and E2 glycoprotein, contains at least one attenuating mutation. The phrases "attenuating mutation" and "attenuating amino acid," as used herein, mean a nucleotide sequence containing a mutation, or an amino acid encoded by a nucleotide sequence containing a mutation, which mutation results in a decreased probability of causing disease in its host (i.e., a loss of virulence), in accordance with standard terminology in the art, See, e.g., B. Davis, et al., *Microbiology* 132 (3d ed. 1980), whether the mutation be a substitution mutation or an in-frame deletion mutation. The phrase "attenuating mutation" excludes mutations or combinations of mutations which would be lethal to the virus. Thus, according to this embodiment, at least one of the first helper RNA and the second helper RNA includes at least one attenuating mutation. In a more preferred embodiment, at least one of the First helper RNA and the second helper RNA includes at least two, or multiple, attenuating mutations. The multiple attenuating mutations may be positioned in either the first helper RNA or in the second helper RNA, or they may be distributed randomly with one or more attenuating mutations being positioned in the first helper RNA and one or more attenuating mutations positioned in the second helper RNA. Alternatively, when the replicon RNA and the RNA encoding the structural proteins not encoded by the first helper RNA are located on the same molecule, an attenuating mutation may be positioned in the RNA which codes for the structural protein not encoded by the first helper RNA. The attenuating mutations may also be located within the RNA encoding non-structural proteins (e.g., the replicon RNA).

Appropriate attenuating mutations will be dependent upon the alphavirus used. For example, when the alphavirus is VEE, suitable attenuating mutations may be selected from the group consisting of codons at E2 amino acid position 76 which specify an attenuating amino acid, preferably lysine, arginine, or histidine as E2 amino acid 76; codons at E2 amino acid position 120 which specify an attenuating amino acid, preferably lysine as E2 amino acid 120; codons at E2 amino acid position 209 which specify an attenuating amino acid, preferably lysine, arginine, or histidine as E2 amino acid 209; codons at E1 amino acid 272 which specify an attenuating mutation, preferably threonine or serine as E1 amino acid 272; codons at E1 amino acid 81 which specify an attenuating mutation, preferably isoleucine or leucine as E1 amino acid 81; codons at E1 amino acid 253 which specify an attenuating mutation, preferably serine or threonine as E1 amino acid 253; and the combination mutation of the deletion of E3 codons 56–59 together with codons at E1 amino acid 253 which specify an attenuating mutation, as provided above. Other suitable attenuating mutations within the VEE genome will be known to those skilled in the art.

In an alternate embodiment, wherein the alphavirus is the South African Arbovirus No. 86 (S.A.AR86), suitable attenuating mutations are located on the RNA molecule encoding both non-structural and structural proteins, and may be selected from the group consisting of codons at nsP1 amino acid position 538 which specify an attenuating amino acid, preferably isoleucine as nsP1 amino acid 538; codons at E2 amino acid position 304 which specify an attenuating amino acid, preferably threonine as E2 amino acid 304; codons at E2 amino acid position 314 which specify an attenuating amino acid, preferably lysine as E2 amino acid 314; codons at E2 amino acid 372 which specify an attenuating amino acid, preferably valine, at E2 amino acid residue 372; codons at E2 amino acid position 376 which specify an attenuating amino acid, preferably alanine as E2 amino acid 376; in combination, codons at E2 amino acid residues 304, 314, 372, and 376 which specify attenuating amino acids at E2 amino acid residues 304, 314, 372, and 376; codons at E2 amino acid position 378 which specify an attenuating amino acid, preferably leucine as E2 amino acid 378; codons at nsP2 amino acid position 96 which specify an attenuating amino acid, preferably glycine as nsP2 amino acid 96; and codons at nsP2 amino acid position 372 which specify an attenuating amino acid, preferably valine as nsP2 amino acid 372; in combination, codons at nsP2 amino acid residues 96 and 372 attenuating substitution mutations at nsP2 amino acid residues 96 and 372; codons at nsP2 amino acid residue 529 which specify an attenuating amino acid, preferably leucine, at nsP2 amino acid residue 529; codons at nsP2 amino acid residue 571 which specify an attenuating amino acid, preferably asparagine, at nsP2 amino acid residue 571; codons at nsP2 amino acid residue 682 which specify an attenuating amino acid, preferably arginine, at nsP2 amino acid residue 682; codons at nsP2 amino acid residue 804 which specify an attenuating amino acid, preferably arginine, at nsP2 amino acid residue 804; codons at nsP3 amino acid residue 22 which specify an attenuating amino acid, preferably arginine, at nsP3 amino acid residue 22; and in combination, codons at nsP2 amino acid residues 529, 571, 682, and 804, and at nsP3 amino acid residue 22, specifying attenuating amino acids at nsP2 amino acid residues 529, 571, 682, and 804, and at nsP3 amino acid residue 22. Suitable attenuating mutations useful in embodiments wherein other alphaviruses are employed are known to those skilled in the art. Attenuating mutations may be introduced into the RNA by performing site-directed mutagenesis on the cDNA which encodes the RNA, in accordance with known procedures. See, Kunkel, *Proc. Natl. Acad. Sci. USA* 82:488 (1985), the disclosure of which is incorporated herein by reference in its entirety. Alternatively, mutations may be introduced into the RNA by replacement of homologous restriction fragments in the cDNA which encodes for the RNA, in accordance with known procedures.

Preferably, the first helper RNA and the second helper RNA also include a promoter. It is also preferred that the replicon RNA also includes a promoter. Suitable promoters for inclusion in the first helper RNA, second helper RNA and replicon RNA are well known in the art. One preferred promoter is the VEE 26S promoter for use when the alphavirus is VEE. Additional promoters beyond VEE 26S include the Sindbis 26S promoter, the Semliki Forest 26S promoter, and any other promoter sequence recognized by alphavirus polymerases. Alphavirus promoter sequences containing mutations which alter the activity level of the promoter (in relation to the activity level of the wild-type) are also suitable in the practice of the present invention. Such mutant promoter sequences are described in in Raju and Huang, *J. Virol.* 65, 2501–2510 (1991), the disclosure of which is incorporated herein in its entirety. In the system wherein the first helper RNA, the second helper RNA, and the replicon RNA are all on separate molecules, the promoters, if the same promoter is used for all three RNAs, provide a homologous sequence between the three molecules. It is preferred that the selected promoter is operative with the non-structural proteins encoded by the replicon RNA molecule.

In cases where vaccination with two immunogens provides improved protection against disease as compared to vaccination with only a single immunogen, a double-promoter replicon would ensure that both imunogens are produced in the same cell. Such a replicon would be the same as the one described above, except that it would contain two copies of the 26S RNA promoter, each followed by a different multiple cloning site, to allow for the insertion and expression of two different heterologous proteins. Another useful strategy is to insert the IRES sequence from the picornavirus, EMC virus, between the two heterologous genes downstream from the single 26S promoter of the replicon described above, thus leading to expression of two immunogens from the single replicon transcript in the same cell.

The infectious, replication defective alphavirus particles may be prepared according to the methods disclosed herein in combination with techniques known to those skilled in the art. The method includes transfecting an alphavirus-permissive cell with a replicon RNA including the alphavirus packaging segment and an inserted heterologous RNA, a first helper RNA including RNA encoding at least one alphavirus structural protein, and a second helper RNA including RNA encoding at least one alphavirus structural protein which is different from that encoded by the first helper RNA; producing the alphavirus particles in the transfected cell; and collecting the alphavirus particles from the cell. The step of transfecting the alphavirus-permissive cell can be carried out according to any suitable means known to those skilled in the art. For example, uptake of the RNA into the cells can be achieved by any suitable means, such as for example, by treating the cells with DEAE-dextran, treating the RNA with "LIPOFECTIN™" before addition to the cells, or by electroporation, with electroporation being the currently preferred means of achieving RNA uptake into the alphavirus-permissive cells. These techniques are well known in the art. See e.g., U.S. Pat. No. 5,185,440 to Davis et al., and PCT Publication No. WO 92/10578 to Bioption AB, the disclosures of which are incorporated herein by reference in their entirety.

The step of facilitating the production of the infectious viral particles in the cells may also be carried out using conventional techniques. See e.g., U.S. Pat. No. 5,185,440 to Davis et al., PCT Publication No. WO 92/10578 to Bioption AB, and U.S. Pat. No. 4,650,764 to Temin et al. (although Temin et al., relates to retroviruses rather than alphaviruses). The infectious viral particles may be produced by standard cell culture growth techniques.

The step of collecting the infectious alphavirus particles may also be carried out using conventional techniques. For example, the infectious particles may be collected by cell lysis, or collection of the supernatant of the cell culture, as is known in the art. See e.g., U.S. Pat. No. 5,185,440 to Davis et al., PCT Publication No. WO 92/10578 to Bioption AB, and U.S. Pat. No. 4,650,764 to Temin et al. Other suitable techniques will be known to those skilled in the art. Optionally, the collected infectious alphavirus particles may be purified if desired. Suitable purification techniques are well known to those skilled in the art.

Pharmaceutical formulations, such as vaccines, of the present invention comprise an immunogenic amount of the infectious, replication defective alphavirus particles as disclosed herein in combination with a pharmaceutically acceptable carrier. An "immunogenic amount" is an amount of the infectious alphavirus particles which is sufficient to evoke an immune response in the subject to which the pharmaceutical formulation is administered. An amount of from about $10^3$ to about $10^7$ replicon-containing particles, and preferably about $10^4$ to $10^6$ replicon-containing particles per dose is believed suitable, depending upon the age and species of the subject being treated, and the immunogen against which the immune response is desired. Exemplary pharmaceutically acceptable carriers include, but are not limited to, sterile pyrogen-free water and sterile pyrogen-free physiological saline solution. Subjects which may be administered immunogenic amounts of the infectious, replication defective alphavirus particles of the present invention include but are not limited to human and animal (e.g., pig, cattle, dog, horse, donkey, mouse, hamster, monkeys) subjects.

Pharmaceutical formulations of the present invention include those suitable for parenteral (e.g., subcutaneous, intradermal, intramuscular, intravenous and intraarticular) administration. Alternatively, pharmaceutical formulations of the present invention may be suitable for administration to the mucus membranes of a subject (e.g., intranasal administration). The formulations may be conveniently prepared in unit dosage form and may be prepared by any of the methods well known in the art.

The helper cells, RNAs and methods of the present invention are useful in in vitro expression systems, wherein the inserted heterologous RNA located on the replicon RNA encodes a protein or peptide which is desirably produced in vitro. The helper cells, RNAs, methods and pharmaceutical formulations of the present invention are additionally useful in a method of administering a protein or peptide to a subject in need of the desired protein or peptide, as a method of treatment or otherwise. In this embodiment of the invention, the heterologous RNA located on the replicon RNA of the present invention encodes the desired protein or peptide, and helper cells or pharmaceutical formulations containing the helper cells of the present invention are administered to a subject in need of the desired protein or peptide. In this manner, the protein or peptide may thus be produced in vivo in the subject. The subject may be in need of the protein or peptide because the subject has a deficiency of the protein or peptide, or because the production of the protein or peptide in the subject may impart some therapeutic effect, as a method of treatment or otherwise.

The following examples are provided to illustrate the present invention, and should not be construed as limiting thereof. In these examples, nm means nanometer, mL means milliliter, IU means infectious units, pfu/mL means plaque forming units/milliliter, VEE means Venezuelan Equine Encephalitis virus, EMC means Encephalomyocarditis virus, BHK means baby hamster kidney cells, HA means hemagglutinin gene, GFP means green fluorescent protein gene, N means nucleocapsid, FACS means fluorescence activated cell sorter, and IRES means internal ribosome entry site. The expression "E2 amino acid (e.g., lys, thr, etc.) number" indicates the designated amino acid at the designated residue of the E2 protein. This convention is also used to refer to amino acids at specific residues in the E1 protein and in the E3 protein.

EXAMPLE 1

Construction of pVR2 Clone

The VEE structural protein genes (C-PE2-6K-E1) were removed from a cDNA clone (pV4031) which contained two attenuating mutations (E2 lys 209, E1 thr 272), and a duplication of the 26S subgenomic RNA promoter sequence immediately downstream from the 3'-end of the E1 glycoprotein gene followed by a multiple cloning site as described in U.S. Pat. No. 5,505,947 to Johnston et al. pV4031 plasmid DNA is digested to completion with ApaI restriction enzyme, which cuts the VEE genomic sequence at nucleotide 7505 (numbered from the 5'-end of the genome sequence). A second recognition site for this enzyme is found in the duplicate 26S subgenomic promoter. Therefore, digestion of pV4031 with ApaI produces two DNA fragments, one containing the VEE nonstructural genes and a single copy of the 26S subgenomic RNA promoter followed by a multiple cloning site, and a second smaller fragment containing a 26S subgenomic RNA promoter followed by the VEE structural genes. The large fragment is isolated and religated to produce the clone, pVR2. FIG. 1 is a graphical representation of the pV4031 clone and pVR2 clone.

EXAMPLE 2

Construction of Single RNA-Helper Plasmids

The starting materials for the helper plasmids are four full-length cDNA clones: pV3000, the virulent Trinidad donkey strain of VEE, and three clones with attenuating mutations, pV3014 (E2 lys 209, E1 thr 272), pV3519 (E2 lys 76, E2 lys 209, E1 thr 272) and pV3526 (deletion of E3 56–59, E1 ser 253), in the genetic background of Trinidad donkey strain VEE. Several different helper plasmids have been made by using unique or rare restriction sites in the full-length cDNA clones to delete portions of the nonstructural protein region. The full-length clone is digested with one or two restriction enzymes, the larger DNA fragment is isolated and then religated to form a functional plasmid. In vitro RNA transcripts from these plasmids upon transfection of tissue culture cells would not encode a functional RNA replication complex, and probably also would not include an encapsidation signal. The helper constructs differ in the size of the nonstructural gene deletion. The helper constructs are designated by the attenuated mutant clone used in their construction, and by the percentage of the nonstructural region deleted. The following helper constructs were generated:

| V3014Δ520-7807 (93%) | V3519Δ520-7507 (93%) | V3526Δ520-7505 (93%) |
|---|---|---|
| V3014Δ520-6965 (87%) | V3519Δ1687-7507 (78%) | V3526Δ520-7505 (93%) |
| V3014Δ2311-7505 (70%) | V3519Δ3958-7507 (47%) | |
| V3014Δ3958-7505 (47%) | V3519Δ1955-7507 (19%) | V3000Δ1955-3359 (19%) |
| V3014Δ520-3954 (46%) | | |
| V3014Δ1955-3359 (19%) | | |
| V3014Δ1951-3359 (19%) | | |
| V3014Δ2311-3055 (10%) | | |
| V3014Δ2307-3055 (10%) | | |

EXAMPLE 3

Construction of Double RNA-Helper Plasmids

Figure 2:
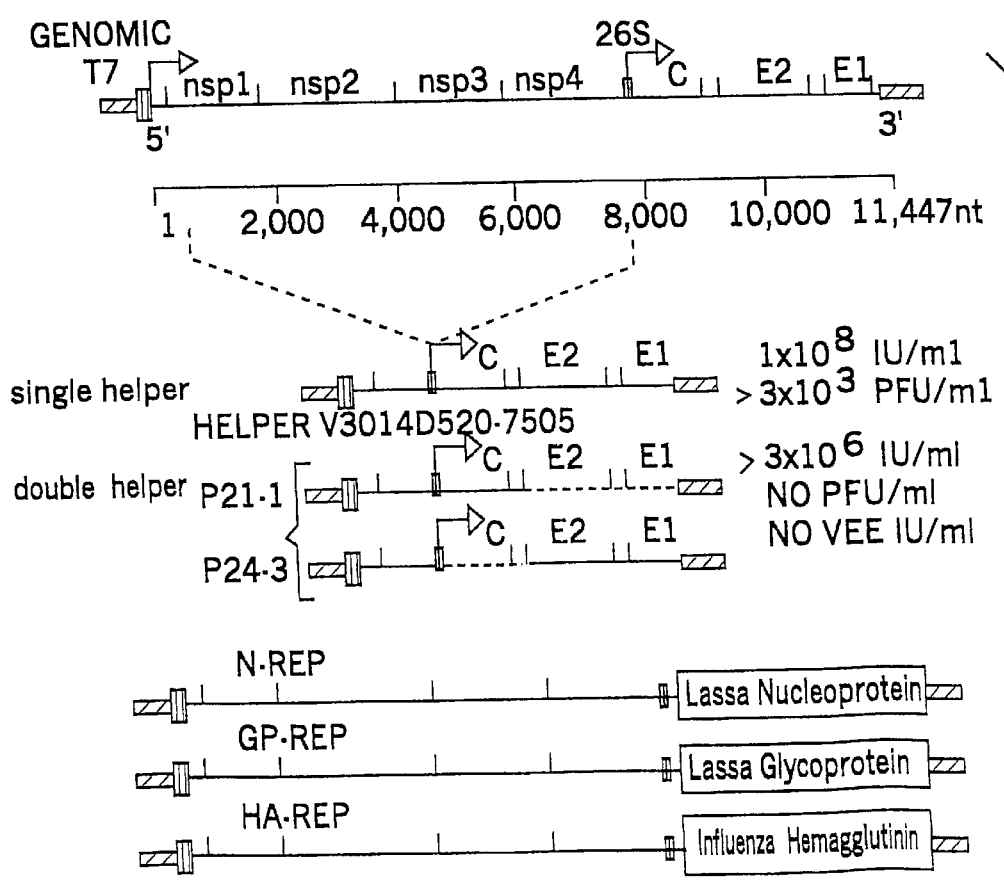
FIG. 2 illustrates the construction of the double helper RNA system plasmids in accordance with the present invention. In the drawings designated P21-1 and P24-3, the dashed lines indicate structural proteins or portions thereof which are deleted in the plasmid.

A plasmid encoding a double helper system also is constructed, as shown in FIG. 2. The V3014Δ520-7505 (93%) single helper clone is used to construct an additional deletion of the E2 and E1 glycoprotein genes by digestion with HpaI restriction enzyme and subsequent ligation, resulting in deletion of the sequence between nucleotide 8494 (in the E3 gene) and nucleotide 11,230 (near the 3'-end of the E1 gene). In vitro RNA transcripts of this plasmid (shown as P21-1 in FIG. 2), when electroporated into BHK cells with a replicon RNA are replicated and transcribed to give a mRNA encoding only the C protein of VEE.

The plasmid encoding the second member of the bipartite helper (shown as P24-3 in FIG. 2) is constructed from the same original clone by cleavage with Tth111I restriction enzyme (at nucleotide 7544) and SpeI restriction enzyme (at nucleotide 8389) and insertion of a synthetic double-stranded oligonucleotide with Tth111I and SpeI termini. The inserted sequence restores the downstream portion of the 26S promoter and an ATG initiation codon followed by a Ser codon, the first amino acid residue of E3. The in vitro RNA transcript of this plasmid when transfected into a cell with replicon RNA will produce the VEE glycoproteins. Co-transfection of both of these helper RNAs into a cell with replicon RNA results in production of infectious but replication-defective particles containing only replicon RNA. Other than the 5' and 3' ends and the 26S promoters (40 nucleotides) of these helper RNAs, the only sequence in common between the capsid and glycoprotein helper RNAs is the sequence from 8389 to 8494 (105 nucleotides).

EXAMPLE 4

Recombinant VEE Replicons Containing Heterologous Genes

The influenza HA gene, the Lassa fever virus N protein gene and the Lassa fever virus envelope glycoprotein gene, have been inserted individually into the pVR2 clone and expressed successfully in cultured BHK cells. These constructs are illustrated in the bottom third portion of FIG. 2. Several other genes, originating from a broad range of organisms including bacteria, protozoae, and invertebrae (e.g., the Botulinum toxin C-fragment gene, the malaria Plasmodium CS1 gene, and the GFP gene cloned from *Aquoria victoria* jellyfish DNA by Chalfie and coworkers, *Science* 263:802 (1994)), have also been successfully inserted into the VEE clone and expressed, as shown below in Table 1. In Table 1, blank entries indicate that the particular function has not yet been tested for that particular gene, not that tests for that function with that gene have been unsuccessful.

TABLE 1

Recombinant VEE Replicons
(Blank Indicates not tested.)

| Family/Virus/Gene | Cloning Shuttle | Status Replicon | Expressed | Function Packaged | Immuno-genic |
|---|---|---|---|---|---|
| Orthomyxoyviruses | | | | | |
| Influenza HA | + | + | + | + | + |
| Arenaviruses | | | | | |
| Lassa N | + | + | + | + | + |
| Lassa GPc | + | + | + | + | |
| Bunyaviruses | | | | | |
| RVFV NSM-G2-G1 | + | + | + | + | |
| CCHF M Seg. | + | + | | | |
| CCHF M 5' half | + | + | + | + | |
| CCHF M 3' half | + | + | + | | |
| SPS NSM-G1-G2 | + | + | | | |
| SFS G2 | + | + | + | | |
| SFS NSm-G1 | + | + | + | + | |
| SFS N | + | + | + | | |
| Filoviruses | | | | | |
| Ebola NP | + | + | + | + | |
| Ebola GP | + | + | + | + | |
| Marburg NP | + | | | | |

TABLE 1-continued

Recombinant VEE Replicons
(Blank Indicates not tested.)

| Family/Virus/Gene | Cloning Shuttle | Status Replicon | Ex-pressed | Function Packaged | Immu-no-genic |
|---|---|---|---|---|---|
| Marburg GP | + | | | | |
| Marburg GPt | + | | | | |
| Poxviruses | | | | | |
| Vaccinia L1 | + | + | + | | |
| Vaccinia D8 | + | + | + | | |
| Lentiviruses | | | | | |
| HIV ma/ca | + | + | + | + | |
| HIV gp160 | + | + | + | | |
| SIV ma/ca | + | + | + | + | |
| SIV gp 160 | + | + | + | | |
| Other | | | | | |
| GFP | + | + | + | | |
| Malaria CSI | + | + | | | |
| Bot-C fragment | + | | | | |

EXAMPLE 5

Detection of Heterologous Protein Expression and Packaging of Infectious Replicon Particles Detection of protein expression in recombinant VEE replicon systems was by specific fluorescent antibody binding, except in the case of GFP, which autofluoresces when exposed to light in the range of 340–490 nm. When GFP-replicon RNA alone is electroporated into BHK cells and expression is assayed by fluorescence, greater than 95% of the cells contain active GFP. Expression levels of Lassa fever N protein in BHK cells are measured following polyacrylamide gel electrophoresis of transfected cell lysates and image analysis with NIH Image Version 1.52 on a Coomassie stained gel. Levels range from 15% to 19% of total cell protein.

GFP is packaged into infectious defective particles by co-electroporation of GFP replicon RNA and V3014Δ520-7505(93%) helper RNA, and the titer is determined by infection of BHK cells and quantitative microscopy under 400 nm light, as well as FACS analysis. The yield of replicon particles is from 2 to $6 \times 10^7$ per mL under these conditions. Yields using various single-helper constructs to package the Lassa fever replicon RNA ranged from $1 \times 10^4$ IU/mL to $8 \times 10^7$ IU/mL.

EXAMPLE 6

Immune Response to Replicons Packaged in Single RNA Helper System

Packaged replicons containing the Lassa fever N gene were inoculated into mice and used to induce serum antibody specific for N. The results are reported in FIG. 3. When a low dose inoculation is used, no serum antibody specific for VEE is detected. However, there is VEE-specific antibody in the serum of a mouse inoculated with a higher dose, probably due to the replication-competent recombinants in the preparation (estimated by a plaque assay to be present at about $10^4$-fold less than the titer of replicon particles). When both types of mice received a second identical dose of N replicon, both showed a significant boost in anti-N titer. See FIG. 3.

EXAMPLE 7

Vaccination with Recombinant VEE Replicons in a Single RNA Helper System

Recombinant VEE replicons were constructed which expressed influenza virus HA (HA-Rep) or Lassa virus N (N-Rep). These replicons were packaged with the VEE single RNA helper system, and yields of $3 \times 10^7$ (HA-RepV) and $4 \times 10^7$ (N-RepV) infectious particles per mL were obtained for the HA and N constructs, respectively. These packaged replicons were inoculated into mice at varying doses, and the resulting immune response was monitored by immunoblots (IB) and enzyme-linked immunoassay (EIA). The mice were then challenged with influenza virus and monitored for sickness and death. The results of this experiment are presented below.

After a single immunization, all mice receiving $3 \times 10^7$ HA-RepV or $4 \times 10^7$ N-RepV seroconverted. In addition, geometric means EIA titers were significantly increased after booster immunizations. All mice receiving $3 \times 10^5$ HA-RepV and $4 \times 10^5$ N-RepV seroconverted after two immunizations. Mice receiving two doses of $3 \times 10^3$ HA-RepV did not seroconvert. All mice receiving two doses of $3 \times 10^7$ or $3 \times 10^5$ HA-RepV were protected against a severe influenza virus challenge. Mice receiving lower doses or control mice receiving saline were not protected.

Because these replicons were packaged with the single RNA helper, approximately 1000 plaque forming units (PFU) of VEE/ml were generated in both the HA-RepV preparations and N-RepV preparations. This resulted in the seroconversion of most of the vaccinated mice to VEE. However, as the helper RNA contained attenuating mutations (the 3014 genetic background), the regenerated VEE virus was attenuated and did not cause disease in these animals.

In order to determine if a prior immunization with one RepV interfered with subsequent immunization with a heterologous Rep V, mice were immunized first with N-RepV and subsequently with HA-RepV, using the single helper RNA system. After two inoculations of either $3 \times 10^6$ or $3 \times 10^4$ N-RepV, inoculation of two doses of $2 \times 10^5$ HA-RepV resulted in seroconversion in all animals to HA. No significant interference from prior immunization with N-RepV was apparent. The subsequent challenge of these animals with virulent influenza virus demonstrated the protective immunity in all animals.

N-RepV was packaged with the single RNA helper which allowed recombination between the replicon and helper RNAs, leading to regeneration of the VEE virus. However, an immune response to HA was induced despite the fact that the animals had developed an antibody response to VEE proteins as a result of the replication-competent VEE virus in the N-RepV preparation.

EXAMPLE 8

Vaccination with Recombinant VEE Replicons Packaged in a Double RNA Helper System As indicated above, the use of a single helper RNA to provide the structural proteins to package the recombinant replicons allows the regeneration of attenuated but fully infectious, replication-competent VEE virus by RNA recombination during co-transfection. To prevent this, a double helper RNA system is constructed in which the nucleocapsid gene is provided on one helper RNA and the glycoprotein genes are provided on a second helper RNA (see Example 3, above). Co-transfections were then carried out with the double helper system and with N-Rep and HA-Rep as above. The yields of packaged replicons, N-RepV and HA-RepV, were monitored by immunofluorescence. The presence or absence of replication-competent VEE virus were similarly monitored by immunofluorescence and by plaque assays (PFU). Media from the co-transfections were also passed into other BHK cell cultures to amplify any infectious VEE virus present; media from these flasks were subsequently assessed by plaque assay. The results are presented below in Table 2.

TABLE 2

Cotransfections with VEE replicons and double helper construct (DH)

|  |  | Immunofluorescence | Plaque assay | |
|---|---|---|---|---|
|  |  | Medium from cotransfected cells | | Infectious virus after amplification in BHK |
| | Date | Rep U/ml[a] | VEE FFU/ml[b] | cells PFU/ml[c] |
| N-Rep + DH | 4/29/95 | $3 \times 10^6$ | <5[d] | <50[d] | None[e] |
|  | 5/14/95 | $5 \times 10^5$ | <5 | <50 | None |
|  | 7/2/95 | $4 \times 10^7$ | <5 | <50 | None |
|  | 7/7/95 | $1 \times 10^8$ | <5 | <50 | None |
| HA-Rep + DH | 5/14/95 | $3 \times 10^5$ | <5 | <50 | None |
|  | 7/2/95 | $4 \times 10^7$ | <5 | <50 | None |
|  | 7/9/95 | $6 \times 10^7$ | <5 | <50 | None |

[a]Replicon units per ml, expressing heterologous gene, by IFA
[b]Focus-forming units, expressing VEE antigen by IFA
[c]Plaque forming units per ml, by plaque assay
[d]Lowest detection limit of assay
[e]1 ml of media from cotransfected cells was used to infect fresh BHK cultures (75 sq cm flask), incubated for 24 and 65 hrs and monitored for infectious virus by plaque assay The data in Table 2 demonstrate that four transfections were carried out with the double helper RNA system and N-Rep and three with this helper system and HA-Rep. Titers of packaged replicons ranged from $3 \times 10^5$ to $1 \times 10^8$. These yields are comparable to, or exceed those achieved with the single helper systems.

In no case were replication-competent VEE virus particles detected by immunofluorescence or by direct plaque assay. This is in marked contrast to results achieved with the single helper system. Replication-competent VEE virus could not be detected even after blind passage (amplification) in fresh cultures of BHK cells, which procedure can theoretically detect a single infectious unit.

Intracerebral (ic) inoculation of newborn mice is usually a more sensitive assay for infectious virus than inoculation of cell cultures. Therefore, HA-RepV packaged with either the single or double RNA systems were inoculated at high doses into suckling mice (Table 3). The VEE glycoprotein genes used to construct both the single helper and double helper systems were obtained from the 3014 VEE construct, which is attenuated in adult mice when inoculated subcutaneously, but not in suckling mice inoculated intracerebrally. The $LD_{50}$ of 3014 in suckling mice is 1.6 PFU.

TABLE 3

Replicon Safety Test - 1C Inoculation of Suckling Mice
Comparison of Influenza HA Replicon Packaged with Single or Double Helper

| Replicon | Infectious Units Inoculated[a] | PFU Present[b] | Percent Survival |
|---|---|---|---|
| Sham Inoculated | 0 | 0 | 100 |
| HA-Double Helper | $5 \times 10^5$ | 0 | 100 |
| HA-Double Helper | $5 \times 10^7$ | 0 | 100 |
| HA-Single Helper | $5 \times 10^5$ | 500 | 10 |
| HA-Single Helper | $5 \times 10^7$ | 50000 | 0 |

[a]Determined as focus forming units by immunofluorescence assay
[b]Determined by plaque assay on vero cells These data indicate that no replication competent VEE virus was detected by plaque assay in the HA-RepV packaged with the double helper RNA system, but relatively high titers were found in the HA-RepV packaged with the single helper system. All suckling mice survived doses of $5 \times 10^5$ and $5 \times 10^7$ HA-RepV packaged with the double helper system, whereas none survived the high dose packaged with the single helper system, and only $\frac{1}{10}$ survived the lower dose.

It will be shown below that a dose of $5 \times 10^7$ HA-RepV packaged with the double helper system is approximately 100 fold more than necessary to achieve an immune response in adult mice inoculated subcutaneously. Therefore, the fact that even the higher dose of packaged HA-RepV/double RNA helper is innocuous in the most sensitive system known (suckling mice) demonstrates the high margin of safety of the double RNA helper system.

EXAMPLE 9

Immunization of Mice With HA Replicons Packaged WIth Double Helper System

N-RepV and HA-RepV produced with the double RNA helper system were inoculated into adult Balb/c mice, and the immune response to Lassa N, influenza HA, and VEE determined by enzyme-linked immunoassay (EIA). The mice were subsequently challenged with virulent influenza virus.

TABLE 4

Influenza HA Replicon packaged with Double Helper System

| | Immunization Schedule | | | Influenza Challenged[d] | |
|---|---|---|---|---|---|
| RepV | Dose[a] | Day PI[b] | VEE PFU[c] | Survive/Total | Sick/Total[e] |
| N-RepV DH | $3 \times 10^6$ | 0 | 0 | | |
| | $3 \times 10^6$ | 32 | 0 | | |
| HA-RepV DH | $2 \times 10^5$ | 84 | 0 | | |
| | $2 \times 10^5$ | 112 | 0 | 6/6 | 0/6 |

| | Serum EIA Titers | | |
|---|---|---|---|
| Day PI | flu-HA | Lassa-N | VEE |
| 14 | <100 | 205 | <100 |
| 84 | nt | 5815 | <100 |

TABLE 4-continued

| | | | |
|---|---|---|---|
| 98 | 4842 | nt | <100 |
| 128 | 20,722 | nt | <100 |

[a]Number of infectious units as determined by immunofluorescence assay
[b]Day post inoculation
[c]Plaque forming units present in inoculum as determined by plaque assay in vero cells
[d]Mice challenged on day 136
[e]Determined visually and by observation of no significant weight loss As the results in Table 4 indicate, no replication-competent VEE virus was detected in either the N-RepV or HA-RepV preparations by plaque assay. After a single inoculation of N-RepV on day 0, mice developed significant titers that were increased dramatically after a booster immunization on day 32. No VEE virus-specific antibody was detected.

The same mice received a subsequent inoculation of HA-RepV on day 84, and responded with significant anti-HA titers when measured on day 98. These geometric mean titers rose to 20,772 following a subsequent inoculation of the HA-RepV. The anti-HA titers demonstrate that there is no interference from prior immunization with a heterologous replicon.

After four inoculations with replicons produced from the double helper system, the mice still had no detectable EIA titer to VEE. The mice were completely protected from a challenge of virulent influenza virus when tested on day 134. This influenza virus had previously caused 50% mortality and 100% morbidity in unvaccinated mice.

EXAMPLE 10

Mutagenesis of Capsid Gene

The alphavirus nucleocapsid and glycoprotein genes of the VEE genome are normally encoded in a single open-reading frame (ORF). During translation of this ORF, the nucleocapsid cleaves itself off the growing polyprotein by virtue of an autoprotease activity. This protease activity is based on an active serine motif similar to that of chymotrypsin, which requires interaction of three distinct amino acid residues (serine, aspartate and histidine). In the VEE nucleocapsid gene, the serine, aspartate and histidine residues are located at amino acids 226, 174, and 152, respectively. Mutagenesis of these residues will compromise the protease activity of the nucleocapsid, and result in non-viable viruses as has been shown for other alphaviruses. However, in the context of the double helper system, in which the nucleocapsid gene is provided on a separate mRNA, there is no requirement for an autoprotease activity.

Experiments were performed to determine whether mutagenesis of these residues would adversely effect packaging in the context of the double helper RNA system. As indicated in Tables 5 and 6 below, site-directed mutagenesis procedures were used to alter the amino acids at three of the loci described above. These mutations were generated in a single helper RNA which encoded the nucleocapsid gene and additional (E3) sequences. Each modified construct was then co-transfected with a replicon, and the size of the nucleocapsid protein was assessed on polyacrylamide gels to determine the extent of protein self-cleavage.

Subsequently, specific combinations of mutations were examined to determine the extent of replicon packaging (as monitored by the release of infectious replicon units). In these studies, a translational termination signal (stop codon) was inserted at the end of the capsid gene.

TABLE 5

Autoprotease activity of the VEE capsid mutants

| Capsid position | Residue | Autoprotease activity |
|---|---|---|
| | A | |
| 152 | H (wt) | + |
| | I | − |
| | D | − |
| | S | − |
| | O | − |
| | G | − |
| | V | − |
| | T | − |
| | A | − |
| | Y | − |
| | R | − |
| | F | − |
| | P | − |
| | B | |
| 174 | D (wt) | + |
| | N | + |
| | A | + |
| | F | − |
| | L | + |
| | K | − |
| | E | + |
| | G | + |
| | T | + |
| | C | + |
| | I | − |
| | S | + |
| | H | + |
| | P | − |
| | V | − |
| | R | − |
| | Y | − |
| | C | |
| 228 | 8 (wt) | + |
| | M | − |
| | Y | − |
| | V | − |
| | R | − |
| | N | − |
| | C | − |
| | Q | − |
| | G | − |
| | H | − |
| | A | − |

TABLE 6

Packaging of VEE replicon by mutant VEE capsid helpers

| Capsid position | Residue | Packaging |
|---|---|---|
| | A | |
| 152 | G | <0 |
| | F | <10 |
| | R | <10 |
| | B | |
| 174** | N | 30 |
| | O | 10 |
| | H | 50 |
| | K | 30 |
| | F | 30 |
| | W | 40 |
| | C | |

TABLE 6-continued

Packaging of VEE replicon by mutant VEE capsid helpers

| Capsid position | Residue | Packaging |
|---|---|---|
| 228 | L | <10 |
|  | R | <10 |
|  | G | 30 |
|  | N | nt |

**%These mutants had also G mutation at position 152
Given 80 percentage assuming 100% packaging with the wild-type VEE capald helper containing G152; D174; and S226, nt = not tested The data in Table 5 illustrate that specific mutations at each of the three loci which prevent nucleocapsid protein self-cleavage were identified. All amino acid substitutions examined at loci 152 or 226 inhibited cleavage. However, a number of different changes at locus 174 permitted cleavage to continue.

The data in Table 6 illustrate that packaging was not detectable with some permutation of mutations. However, for others, efficient packaging was observed comparable to wild-type VEE nucleocapsid helpers. Therefore, in the unlikely event that a multiple recombination event would occur among a replicon and each of the double-helper RNA system RNAs, use of such modified nucleocapsid constructs could prevent the recombinant from possessing a functional nucleocapsid gene. The modified nucleocapsid genes as described herein are functional only in the context of the double helper system.

The nucleocapsid protein altered as above provides additional assurance that recombination to produce the replication-competent virus will not occur. The altered capsid protein gene that functions in the particle assembly but not in autoproteolysis would provide helper function for production of replicon particles, but would be very unlikely to produce a viable recombinant.

The foregoing is illustrative of the present invention and is not to be construed as limiting thereof, the invention is defined by the following claims, with equivalents or the claims to be included therein.

That which is claimed is:

1. A composition comprising a population of infectious, defective alphavirus particles,
    wherein each particle comprises Venezuelan Equine Encephalitis virus (VEE) structural proteins and an alphavirus replicon RNA, and
    wherein said replicon RNA comprises an alphavirus packaging signal, one or more heterologous RNA sequence(s) encoding an immunogen, and wherein said replicon RNA lacks sequences encoding alphavirus structural proteins; and further
    wherein said population contains no detectable replication-competent alphavirus particles as determined by passage on permissive cells in culture,
    and further wherein at least one of said VEE structural proteins comprises one or more attenuating mutations selected from the group consisting of an attenuating mutation at E1 amino acid position 81, an attenuating mutation at E1 amino acid position 253, an attenuating mutation at E1 amino acid position 272, an attenuating mutation at E2 amino acid position 76, an attenuating mutation at E2 amino acid position 120, an attenuating mutation at E2 amino acid position 209, and the deletion of E3 amino acids 56–59.

2. The composition of claim 1, wherein said heterologous RNA sequence consists of one heterologous RNA sequence.

3. The composition of claim 1, wherein said replicon RNA comprises two different heterologous RNA sequences.

4. The composition of claim 3, wherein said two different heterologous RNA sequences each encode a different immunogenic protein or peptide.

5. The composition of claim 1, wherein said alphavirus replicon RNA comprises a promoter sequence which directs the expression of a first heterologous RNA sequence and an IRES sequence positioned upstream of a second heterologous RNA sequence.

6. The composition of claim 1, wherein said alphavirus replicon RNA comprises two separate promoter sequences, each of which directs the expression of a different heterologous RNA sequence.

7. The composition of claim 6, wherein said two separate promoter sequences are alphavirus 26S promoter sequences.

8. The composition of claim 1, wherein the capsid protein of said alphavirus particles has reduced autoproteolytic activity.

9. The composition of claim 1, wherein said permissive cells are Baby Hamster Kidney cells.

10. The composition of claim 1, wherein said VEE structural proteins of said alphavirus particles comprise an attenuating mutation at E1 amino acid position 81.

11. The composition of claim 1, wherein said VEE structural proteins of said alphavirus particles comprise an attenuating mutation at E1 amino acid position 253.

12. The composition of claim 1, wherein said VEE structural proteins of said alphavirus particles comprise an attenuating mutation at E1 amino acid position 81 and an attenuating mutation at E1 amino acid position 253.

13. A pharmaceutical formulation comprising the composition of claim 1 in a pharmaceutically acceptable carrier.

14. A composition comprising a population of infectious, defective Venezuelan Equine Encephalitis virus (VEE) particles,
    wherein each particle comprises VEE structural proteins and a VEE replicon RNA, and
    wherein said replicon RNA comprises an alphavirus packaging signal, one or more heterologous RNA sequence(s) encoding an immunogen, and wherein said replicon RNA lacks sequences encoding alphavirus structural proteins; and further
    wherein said population contains no detectable replication-competent VEE particles as determined by passage on permissive cells in culture,
    and further wherein at least one of said VEE structural proteins comprises one or more attenuating mutations selected from the group consisting of an attenuating mutation at E1 amino acid position 81, an attenuating mutation at E1 amino acid position 253, an attenuating mutation at E1 amino acid position 272, an attenuating mutation at E2 amino acid position 76, an attenuating mutation at E2 amino acid position 120, an attenuating mutation at E2 amino acid position 209, and the deletion of E3 amino acids 56–59.

15. A pharmaceutical formulation comprising the composition of claim 14 in a pharmaceutically acceptable carrier.

16. A method of producing an immune response in a subject, comprising administering to the subject an effective amount of the pharmaceutical formulation of claim 13.

17. The method of claim 16, wherein the subject is a mammal.

18. The method of claim 16, wherein the subject is a human.

19. The method of claim 16, wherein the subject is a horse.

20. The method of claim 16, wherein the composition is administered by a method selected from the group consisting of subcutaneous, intradermal, intramuscular, intravenous, intraarticular, and intranasal administration.

21. The method of the claim 16, wherein heterologous RNA sequence consists of one heterologous RNA sequence.

22. The method of claim 16, wherein the replicon RNA comprises two different heterologous RNA sequences.

23. The method of claim 22, wherein the two different heterologous RNA sequences each encode a different immunogenic protein or peptide.

24. The method of claim 16, wherein the alphavirus replicon RNA comprises a promoter sequence which directs the expression of a first heterologous RNA sequence and an IRES sequence positioned upstream of a second heterologous RNA sequence.

25. The method of claim 16, wherein the alphavirus replicon RNA comprises two separate promoter sequences, each of which directs the expression of a different heterologous RNA sequence.

26. The method of claim 25, wherein the two separate promoter sequences are alphavirus 26S promoter sequences.

27. The method of claim 16, the capsid protein of the alphavirus particles has reduced autoproteolytic activity.

28. The method of claim 16, wherein the permissive cells are Baby Hamster Kidney cells.

29. The method of claim 16, wherein the VEE structural proteins of the alphavirus particles comprise an attenuating mutation at E1 amino acid position 81.

30. The method of claim 16, wherein the VEE structural proteins of the alphavirus particles comprise an attenuating mutation at E1 amino acid position 253.

31. The method of claim 16, wherein the VEE structural proteins of the alphavirus particles comprise an attenuating mutation at E1 amino acid position 81 and an attenuating mutation at E1 amino acid position 253.

32. A method of producing an immune response in a subject, comprising administering to the subject an effective amount of the pharmaceutical formulation of claims 15.

33. A composition comprising a population of infectious, defective alphavirus particles,
   wherein each particle comprises South African Arbovirus No. 86 (S.A.AR86) structural proteins and an alphavirus replicon RNA, and
   wherein said replicon RNA comprises an alphavirus packaging signal, one or more heterologous RNA sequence(s) encoding an immunogen, and wherein said replicon RNA lacks sequences encoding alphavirus structural proteins; and further
   wherein said population contains no detectable replication-competent alphavirus particles as determined by passage on permissive cells in culture,
   and further wherein at least one of said S.A.AR86 structural proteins comprises one or more attenuating mutations selected from the group consisting of an attenuating mutation at E2 amino acid position 304, an attenuating mutation at E2 amino acid position 314, an attenuating mutation at E2 amino acid position 372, an attenuating mutation at E2 amino acid position 376, and an attenuating mutation at E2 amino acid position 378.

34. A pharmaceutical formulation comprising the composition of claim 33 in a pharmaceutically acceptable carrier.

35. A composition comprising a population of infectious, defective alphavirus particles,
   wherein each particle comprises alphavirus structural proteins and a South African Arbovirus No. 86 (S.A.AR86) replicon RNA, and
   wherein said replicon RNA comprises an alphavirus packaging signal, one or more heterologous RNA sequence(s) encoding an immunogen, and wherein said replicon RNA lacks sequences encoding alphavirus structural proteins; and further
   wherein said population contains no detectable replication-competent alphavirus particles as determined by passage on permissive cells in culture,
   and further wherein at least one nonstructural protein encoded by said replicon RNA comprises one or more attenuating mutations selected from the group consisting of an attenuating mutation at nsP1 amino acid position 538, an attenuating mutation at nsP2 amino acid position 96, an attenuating mutation at nsP2 amino acid position 372, an attenuating mutation at nsP2 amino acid position 529, an attenuating mutation at nsP2 amino acid position 571, an attenuating mutation at nsP2 amino acid position 682, an attenuating mutation at nsP2 amino acid position 804, and an attenuating mutation at nsP3 amino acid position 22.

36. A pharmaceutical formulation comprising the composition of claim 35 in a pharmaceutically acceptable carrier.

37. The composition of claim 35, wherein said replicon RNA encodes a S.A.AR86 nsP1 protein comprising an attenuating mutation at amino acid position 538.

38. A composition comprising a population of infectious, defective South African Arbovirus No. 86 (S.A.AR86) particles,
   wherein each particle comprises S.A.AR86 structural proteins and a S.A.AR86 replicon RNA, and
   wherein said replicon RNA comprises an alphavirus packaging signal, one or more heterologous RNA sequence(s) encoding an immunogen, and wherein said replicon RNA lacks sequences encoding alphavirus structural proteins; and further
   wherein said population contains no detectable replication-competent S.A.AR86 particles as determined by passage on permissive cells in culture,
   and further wherein at least one nonstructural protein encoded by said replicon RNA or at least one structural protein of said S.A.AR86 particles comprises one or more attenuating mutations selected from the group consisting of an attenuating mutation at nsP1 amino acid position 538, an attenuating mutation at nsP2 amino acid position 96, an attenuating mutation at nsP2 amino acid position 372, an attenuating mutation at nsP2 amino acid position 529, an attenuating mutation at nsP2 amino acid position 571, an attenuating mutation at nsP2 amino acid position 682, an attenuating mutation at nsP2 amino acid position 804, an attenuating mutation at nsP3 amino acid position 22, an attenuating mutation at E2 amino acid position 304, an attenuating mutation at E2 amino acid position 314, an attenuating mutation at E2 amino acid position 372, an attenuating mutation at E2 amino acid position 376, and an attenuating mutation at E2 amino acid position 378.

39. A pharmaceutical formulation comprising the composition of claim 38 in a pharmaceutically acceptable carrier.

40. The composition of claim 38, wherein said replicon RNA encodes a S.A.AR86 nsP1 protein comprising an attenuating mutation at amino acid position 538.

41. A method of producing an immune response in a subject, comprising administering to the subject an effective amount of the pharmaceutical formulation of claim 34.

42. A method of producing an immune response in a subject, comprising administering to the subject an effective amount of the pharmaceutical formulation of claim 36.

43. A method of producing an immune response in a subject, comprising administering to the subject an effective amount of the pharmaceutical formulation of claim 39.

44. A composition comprising a population of infectious, defective alphavirus particles, wherein each particle comprises alphavirus structural proteins and an alphavirus replicon RNA, and wherein the capsid protein of said alphavirus particles has reduced autoproteolytic activity, and further wherein said replicon RNA comprises an alphavirus packaging signal, one or more heterologous RNA sequence (s) encoding an immunogen, and wherein said replicon RNA lacks sequences encoding alphavirus structural proteins.

45. A pharmaceutical formulation comprising the composition of claim 44 in a pharmaceutically acceptable carrier.

46. The composition of claim 44, wherein said population contains no detectable replication-competent alphavirus particles as determined by passage on permissive cells in culture.

47. The composition of claim 44, wherein said alphavirus particles comprise one or more attenuating mutations.

48. The composition of claim 44, wherein said alphavirus structural proteins are Venezuelan Equine Encephalitis (VEE) virus structural proteins.

49. The composition of claim 48, wherein the capsid protein of said alphavirus particles comprises one or more mutations selected from the group consisting of a mutation at amino acid position 152, amino acid position 174, and amino acid position 226.

50. A method of producing an immune response in a subject, comprising administering to the subject an effective amount of the pharmaceutical formulation of claim 45.

51. A composition comprising a population of infectious, defective alphavirus particles, wherein each particle comprises alphavirus structural proteins and an alphavirus replicon RNA, and wherein said replicon RNA comprises an alphavirus packaging signal, one or more heterologous RNA sequence (s) encoding an immunogen selected from the group consisting of an arenavirus immunogen, a lentivirus immunogen, a poxvirus immunogen, a filovirus immunogen, an orthomyxovirus immunogen, a bunyavirus immunogen, a coronavirus immunogen, a malaria immunogen and a Clostridium immunogen and wherein said replicon RNA lacks sequences encoding alphavirus structural proteins; and further wherein said population contains no detectable replication-competent alphavirus particles as determined by passage on permissive cells in culture, and further wherein said alphavirus particles comprise one or more attenuating mutations.

52. A pharmaceutical formulation comprising the composition of claim 51, in a pharmaceutically acceptable carrier.

53. The composition of claim 51, wherein said immunogen is a Lassa fever virus immunogen.

54. The composition of claim 53, wherein said immunogen is a Lassa fever virus nucleocapsid protein or an envelope glycoprotein immunogen.

55. The composition of claim 51, wherein said immunogen is a Human Immunodeficiency Virus immunogen.

56. The composition of claim 55, wherein said immunogen is selected from the group consisting of a Human Immunodeficiency Virus matrix protein, capsid protein, and gp160 immunogen.

57. The composition of claim 49, wherein said immunogen is a Simian Immunodeficiency Virus immunogen.

58. The composition of claim 54, wherein said immunogen is selected from the group consisting of a Simian Immunodeficiency Virus matrix protein, capsid protein, and gp160 immunogen.

59. The composition of claim 51, wherein said immunogen is a vaccinia virus immunogen.

60. The composition of claim 59, wherein said immunogen is a vaccinia virus L1 or D8 immunogen.

61. The composition of claim 51, wherein said immunogen is an Ebola virus immunogen.

62. The composition of claim 61, wherein said immunogen is an Ebola virus nucleoprotein or glycoprotein immunogen.

63. The composition of claim 51, wherein said immunogen is a Marburg virus immunogen.

64. The composition of claim 63, wherein said immunogen is a Marburg virus nucleoprotein or glycoprotein immunogen.

65. The composition of claim 51, wherein said immunogen is an influenza virus immunogen.

66. The composition of claim 65, wherein said immunogen is an influenza virus HA immunogen.

67. The composition of claim 51, wherein said immunogen is a Rift Valley Fever Virus (RVFV) immunogen.

68. The composition of claim 67, wherein said immunogen is selected from the group consisting of a RVFV G2 glycoprotein, G1 glycoprotein, and M segment nonstructural protein immunogen.

69. The composition of claim 51, wherein the immunogen is a Crimean-Congo hemorrhagic fever virus (CCHF) immunogen.

70. The composition of claim 69, wherein the immunogen is selected from the group a CCHF G2 glycoprotein, G1 glycoprotein, and M segment nonstructural protein immunogen.

71. The composition of claim 51, wherein the immunogen is a Sicilian Sandfly Fever virus (SFS) immunogen.

72. The composition of claim 71, wherein the immunogen is selected from the group consisting of a G2 glycoprotein, G1 glycoprotein, M segment nonstructural protein, and nucleocapsid immunogen.

73. The composition of claim 51, wherein the immunogen is a human coronavirus immunogen.

74. The composition of claim 73, wherein the immunogen is a human coronavirus envelope glycoprotein immunogen.

75. The composition of claim 51, wherein the immunogen is an Equine Infectious Anemia virus immunogen.

76. The composition of claim 51, wherein the immunogen is a Plasmodium CS1 immunogen.

77. The composition of claim 51, wherein the immunogen is a Botulinum toxin C fragment immunogen.

78. A method of producing an immune response in a subject, comprising administering to the subject an effective amount of the pharmaceutical formulation of claim 52.

* * * * *

UNITED STATES PATENT AND TRADEMARK OFFICE
CERTIFICATE OF CORRECTION

PATENT NO. : 6,521,235 B2
DATED : February 18, 2003
INVENTOR(S) : Johnston et al.

It is certified that error appears in the above-identified patent and that said Letters Patent is hereby corrected as shown below:

Column 21,
Line 7, Claim 21 should read as follows:

21. The method of the claim 16, wherein the heterologous RNA sequence consists of one heterologous RNA sequence.

Line 24, should read as follows:
    27. The method of claim 16, wherein the capsid protein of the Column 24,
Line 41, should read as follows:
    -- is selected from the group consisting of a CCHF G2 glycoprotein, G1 --

Signed and Sealed this

Ninth Day of September, 2003

JAMES E. ROGAN
*Director of the United States Patent and Trademark Office*